United States Patent
Parker

(10) Patent No.: US 8,633,016 B2
(45) Date of Patent: Jan. 21, 2014

(54) MICROBIAL DETECTION ASSEMBLY

(75) Inventor: Jonathan G. Parker, Debary, FL (US)

(73) Assignee: Covidien LP, Mansfield, MA (US)

( * ) Notice: Subject to any disclaimer, the term of this patent is extended or adjusted under 35 U.S.C. 154(b) by 732 days.

(21) Appl. No.: 12/565,165

(22) Filed: Sep. 23, 2009

(65) Prior Publication Data
US 2010/0081166 A1    Apr. 1, 2010

Related U.S. Application Data

(60) Provisional application No. 61/101,387, filed on Sep. 30, 2008.

(51) Int. Cl.
| | |
|---|---|
| *C12M 3/00* | (2006.01) |
| *C12M 1/34* | (2006.01) |
| *G01N 1/00* | (2006.01) |
| *A61M 37/00* | (2006.01) |
| *A61M 5/00* | (2006.01) |
| *A61M 5/315* | (2006.01) |
| *A61B 19/00* | (2006.01) |

(52) U.S. Cl.
USPC .......... 435/287.6; 435/287.5; 435/288.1; 436/174; 604/87; 604/110; 604/208; 604/231; 604/407

(58) Field of Classification Search
USPC .......... 435/287.6, 287.5, 288.1, 283.1–309.4; 436/174; 604/87, 110, 208, 231, 407
See application file for complete search history.

(56) References Cited

U.S. PATENT DOCUMENTS

| | | | |
|---|---|---|---|
| 3,508,653 A | | 4/1970 | Coleman |
| 3,586,064 A | * | 6/1971 | Brown et al. ............... 141/1 |
| 3,882,021 A | * | 5/1975 | Ayres ....................... 210/136 |
| 4,192,919 A | * | 3/1980 | Raghavachari ........... 600/577 |
| 4,314,029 A | | 2/1982 | Ohtake et al. |
| 4,409,988 A | | 10/1983 | Greenspan |
| 4,952,498 A | | 8/1990 | Waters |
| 5,047,331 A | * | 9/1991 | Swaine et al. ............ 435/29 |
| 5,051,360 A | | 9/1991 | Waters |
| 5,098,842 A | | 3/1992 | Nakajima et al. |

(Continued)

FOREIGN PATENT DOCUMENTS

| | | |
|---|---|---|
| EP | 0124193 | 11/1984 |
| EP | 0340902 A1 | 11/1989 |

(Continued)

OTHER PUBLICATIONS

EP Search Report Application No. EP 09 17 1237 dated Jun. 8, 2011.

(Continued)

*Primary Examiner* — Nathan Bowers
*Assistant Examiner* — Lydia Edwards
(74) *Attorney, Agent, or Firm* — Lisa E. Winsor, Esq.

(57) ABSTRACT

A microbial detection assembly is disclosed which includes a tubular body, a pierceable septum, and a plunger. The tubular body defines a longitudinal axis and has a first end and a second end. The pierceable septum is configured to seal the first end of the tubular body. The plunger head is configured to substantially close the second end of the tubular body. Together, the plunger head, the pierceable septum, and the tubular body define a reservoir dimensioned to receive a medium and a sample substance. Additionally, the plunger head is positioned and is movable within the tubular body in response to changes in pressure within the reservoir.

2 Claims, 7 Drawing Sheets

(56) References Cited

U.S. PATENT DOCUMENTS

| | | | |
|---|---|---|---|
| 5,240,322 A | 8/1993 | Haber et al. | |
| 5,292,318 A * | 3/1994 | Haber et al. | 604/407 |
| 5,310,658 A | 5/1994 | Berndt | |
| 5,518,923 A | 5/1996 | Berndt et al. | |
| 5,536,253 A * | 7/1996 | Haber et al. | 604/110 |
| 5,707,823 A | 1/1998 | Carr et al. | |
| 5,869,329 A | 2/1999 | Berndt | |
| 6,150,159 A | 11/2000 | Fry | |
| 2004/0166556 A1 | 8/2004 | Cullimore | |
| 2005/0031493 A1* | 2/2005 | Kipke et al. | 422/99 |
| 2006/0110292 A1* | 5/2006 | Deverse et al. | 422/68.1 |
| 2006/0292650 A1* | 12/2006 | Braig et al. | 435/14 |
| 2008/0082055 A1 | 4/2008 | Lloyd et al. | |
| 2009/0036764 A1* | 2/2009 | Rivas et al. | 600/365 |

FOREIGN PATENT DOCUMENTS

| | | |
|---|---|---|
| EP | 0597584 A1 | 5/1994 |
| WO | WO 93/03178 | 2/1993 |
| WO | WO 2007/092586 | 8/2007 |

OTHER PUBLICATIONS

Japanese Office Action dated Sep. 25, 2013 in Japanese Appln. No. 2009/225634.

* cited by examiner

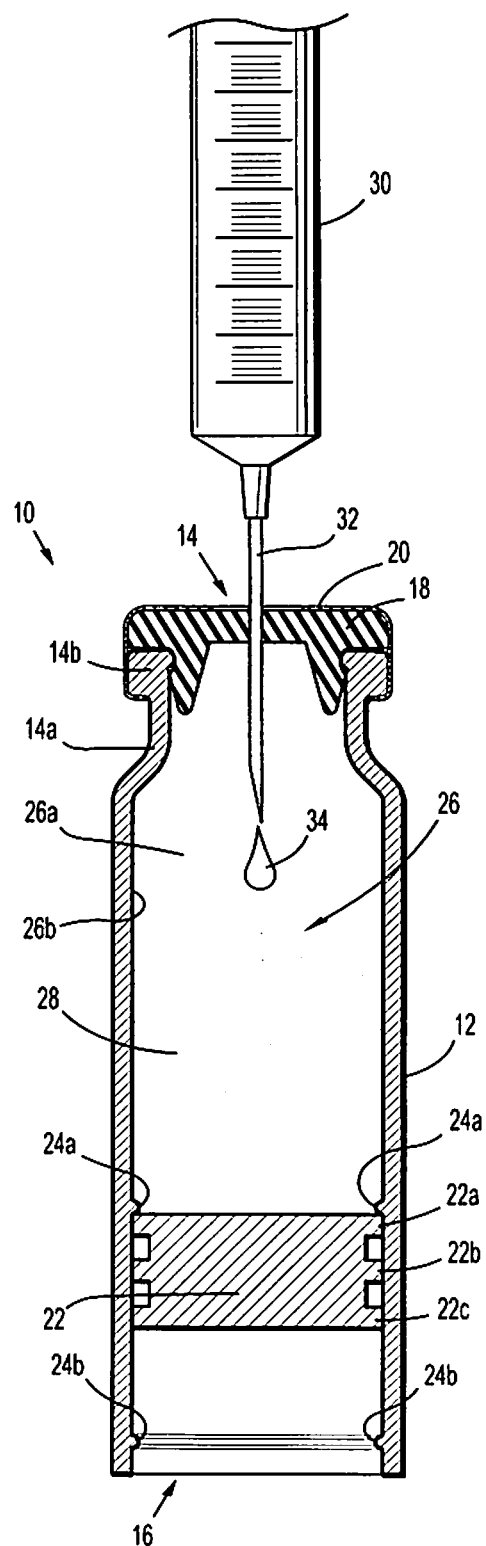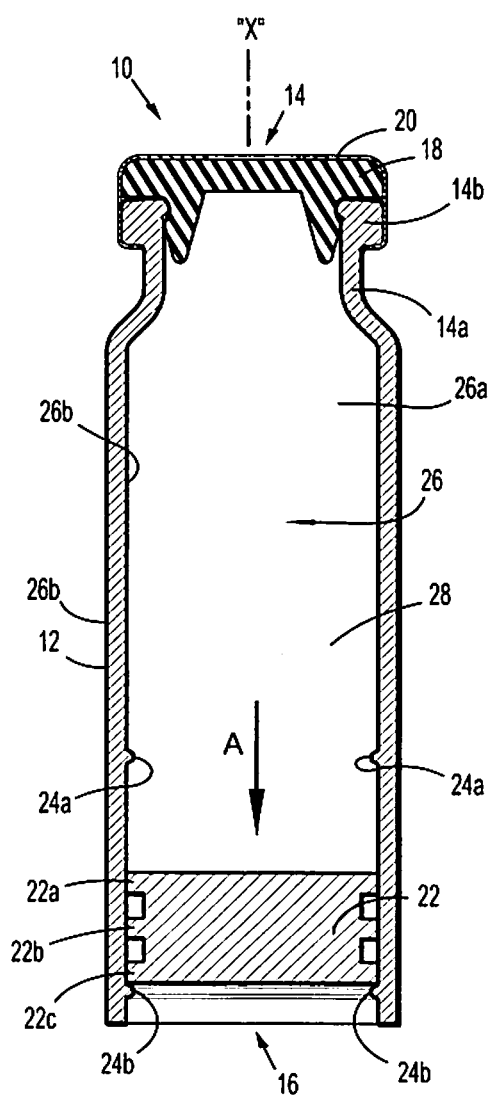
FIG. 4  FIG. 5

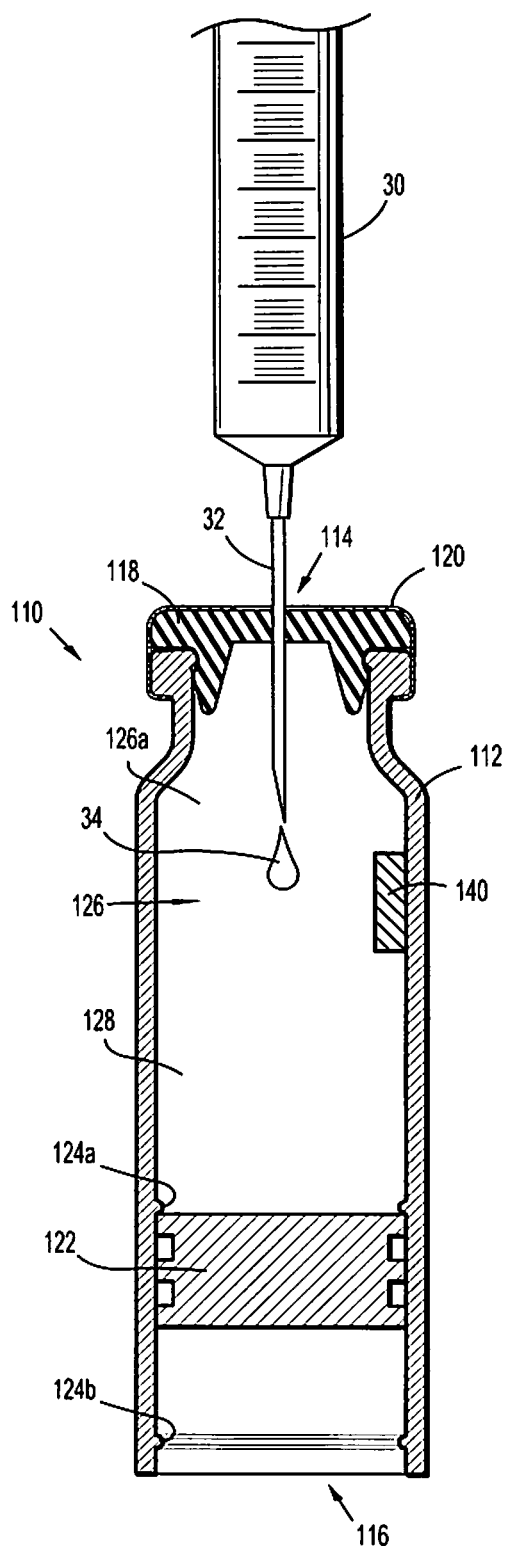
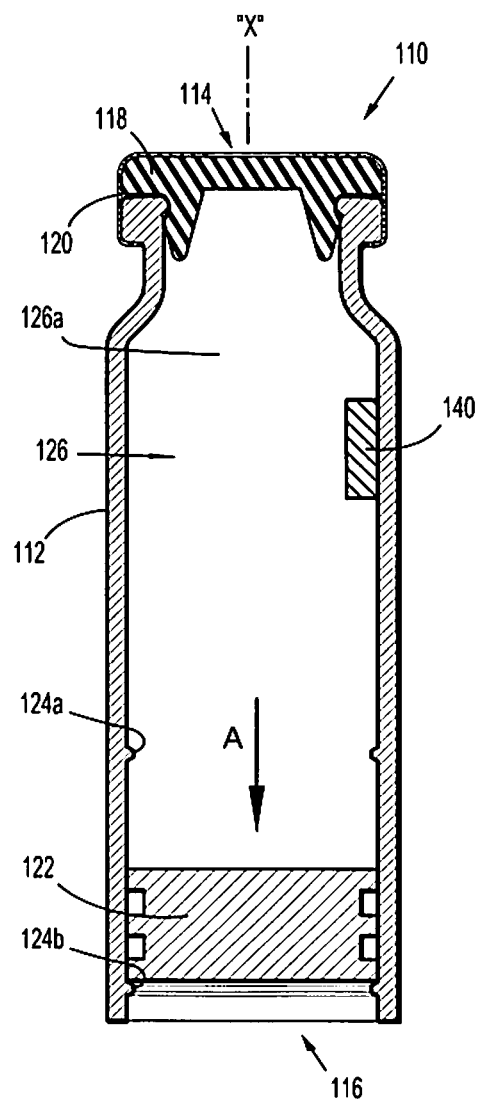
FIG. 6  FIG. 7

MICROBIAL DETECTION ASSEMBLY

CROSS-REFERENCE TO RELATED APPLICATIONS

The present application claims the benefit of and priority to U.S. Provisional Patent Application No. 61/101,387, filed on Sep. 30, 2008, which is incorporated herein by reference in its entirety.

BACKGROUND

1. Technical Field

The present disclosure relates to the field of medical fluid devices, in particular, a microbial detection assembly for detecting microbial contents of a sample substance.

2. Description of Related Art

In the medical field, a common medical procedure is to test for the presence of bacteria in a patient's body fluids, particularly blood. Traditionally, a blood culture vial having a bacterial growth medium (e.g., soy broth) and head space (e.g., nitrogen or oxygen) is provided and a small quantity of blood is injected through a pierceable septum into vial. The vial is incubated at a specified temperature and monitored for bacterial growth. If the blood contains bacteria, the bacterial growth generates carbon dioxide. Monitoring the carbon dioxide content can be accomplished by methods well established in the art, including radiochemical, infrared absorption at a carbon dioxide spectral line, or pressure/vacuum measurement.

Upon determination of a positive blood sample (i.e., blood containing bacteria) a clinician may need to withdraw the positive blood sample to perform further medical examinations. Withdrawal and transfer of a positive blood sample from a known blood culture vial can be cumbersome and typically requires insertion of a syringe needle into the pierceable septum for subsequent withdrawal of the sample into a transfer syringe followed by removal of the sample from the transfer syringe. Use of the transfer syringe and syringe needle increases the risk of an accidental needle stick to a clinician and potential contamination of the blood.

SUMMARY

A microbial detection assembly is disclosed which includes a tubular body, a pierceable septum, and a plunger. The tubular body defines a longitudinal axis and has a first end and a second end. The pierceable septum is configured to seal the first end of the tubular body. The plunger head is configured to substantially close the second end of the tubular body. Together, the plunger head, the pierceable septum, and the tubular body define a reservoir dimensioned to receive a medium and a sample substance. Additionally, the plunger head is positioned and is movable within the tubular body in response to changes in pressure within the reservoir.

In embodiments, a securing structure is configured to secure the pierceable septum to the first end of the tubular body. The securing structure may be constructed from metal, plastic, or epoxy. In addition, the securing structure may be fastened to the end of the tubular body by either crimping, screwing, pressing, gluing, or welding.

In embodiments, the microbial detection assembly includes a first retaining structure and a second retaining structure that are disposed within the tubular body. In this configuration, the plunger head is movable along the longitudinal axis between a first position and a second position that is defined by the first and second retaining structures during a microbial detection period.

The tubular body may be constructed from plastic or glass. The pierceable septum may be constructed from rubber composites, silicone composites, or gel composites. In addition, the tubular body defines a neck portion that has an annular flange portion, which terminates into the first end of the tubular body.

The plunger head includes a plurality of annular ribs which are disposed annularly about the plunger head. The annular ribs are positioned to slidably and sealingly engage with an inner wall of the tubular body.

In embodiments, the tubular body and the plunger head has a lubricous material. The first and second retaining structures may be annular rings or injection molded nubs. In addition, the plunger head may be movable along the longitudinal axis beyond the first retaining structure to a third position adjacent the neck portion of the tubular body.

In embodiments, the microbial detection assembly includes a sensor that is configured to indicate levels of carbon dioxide within the reservoir of the tubular body. The sensor may be a colorimetric sensor.

In embodiments, the microbial detection assembly includes a plunger rod that has an elongate plunger shaft adapted to releasably engage the plunger head. The plunger rod and the plunger head are movable along the longitudinal axis to dispense the medium and the sample substance from within the reservoir. In addition, the microbial detection assembly may further include a needle assembly that is mounted on the first end of the tubular body.

BRIEF DESCRIPTION OF THE DRAWINGS

Various embodiments of the presently disclosed microbial detection assembly are disclosed herein with reference to the drawings, wherein:

FIG. 4 is a side cross-sectional view of the microbial detection assembly shown in FIG. 1 showing a plunger head disposed in a first position with a syringe assembly inserted therein;

FIG. 5 is a side cross-sectional view of the microbial detection assembly shown in FIG. 1 showing a plunger head disposed in a second position;

FIG. 6 is a side cross-sectional view of another embodiment of the presently disclosed microbial detection assembly having a sensor showing a plunger head disposed in a first position with a syringe assembly inserted therein;

FIG. 7 is a side cross-sectional view of the microbial detection assembly of FIG. 6 having a sensor showing the plunger head disposed in a second position;

DETAILED DESCRIPTION

Figure 1:
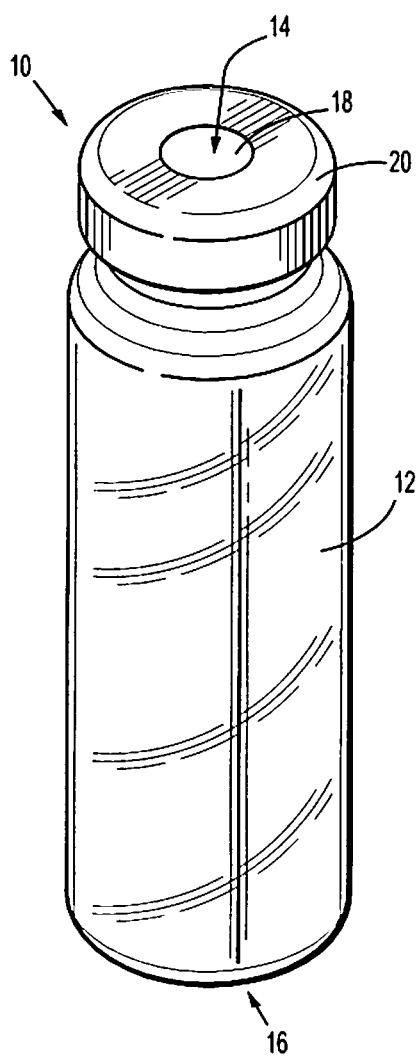
FIG. 1 is a perspective view of one embodiment of the presently disclosed microbial detection assembly.
Figure 2:
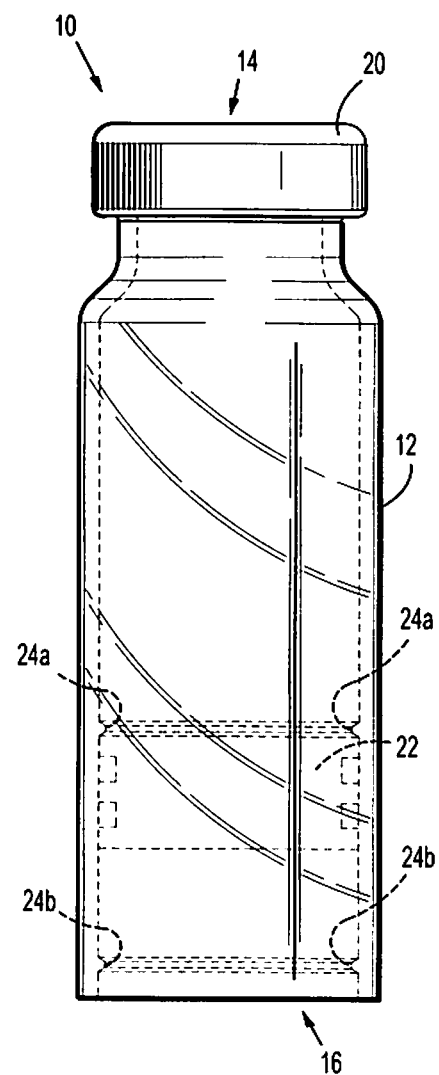
FIG. 2 is a side elevational view of the microbial detection assembly shown in FIG. 1.
Figure 3:
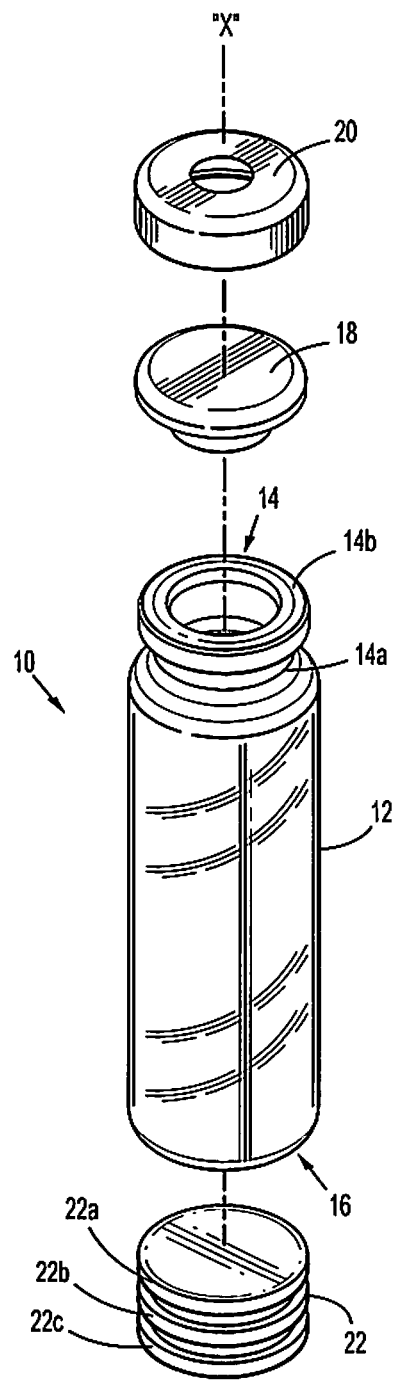
FIG. 3 is an exploded perspective view of the microbial detection assembly shown in FIG. 1.

Referring initially to FIGS. 1-5, a microbial detection assembly, which may also be referred to as a blood culture vial, is generally depicted as numeral 10. Microbial detection assembly 10, generally, includes a tubular body 12, a septum 18 and a plunger head 22, which together define a reservoir 26. The reservoir 26 is configured to contain a bacterial growth medium 28 having a head space 26a including nitrogen and/or oxygen and a sample substance 34, e.g., blood. Briefly, if the blood contains bacteria, bacterial growth will occur. The bacterial growth generates carbon dioxide, which results in a pressure increase within reservoir 26. As a result, plunger head 22 moves within tubular body 12 towards a bottom end 16 of tubular body during a microbial detection period, indicating to a clinician that bacteria is present in the blood. A more detailed description of the aforementioned arrangement will be discussed further below.

FIGS. 4 and 5 depict the tubular body 12 having a top end 14 and a bottom end 16. Tubular body 12 may be made of a material including, but not limited to, plastic, glass, or any other suitable container material. Microbial detection assembly 10 further includes a septum 18 configured to close, i.e. seal, the open first end 14 of the tubular body 12.

Septum 18 is pierceable such that a sharp object, for example, a needle 32 of a syringe assembly 30 (as shown in FIG. 4), can penetrate through the surface of the septum 18 and into reservoir 26 of tubular body 12. In this manner, syringe assembly 30 allows a clinician to deposit a sample substance 34, for example, blood, into reservoir 26. When the syringe assembly 30 is removed from the tubular body 12 (as shown in FIG. 5), the septum 18, which is constructed from a resilient material, seals reservoir 26. The pierceable septum 18 may be made of a suitable pierceable resilient material including, but not limited to, rubber, silicone, gel, or the like.

The top end 14 of tubular body 12 defines a neck portion 14a which includes an annular flange portion 14b. Septum 18 is tightly held in place over top end 14 by a securing structure 20. Securing structure 20 may include an annular aluminum crimp that is crimped around top end 14 and further extends under the annular flange portion 14b. Alternatively, the securing structure 20 may be any suitable securing material, including, but not limited to, metal, plastic, epoxy, or the like. It is also envisioned that securing structure 20 may be fastened to the top end 14 by any suitable fastening technique including, but not limited to, crimping, screwing, pressing, gluing, welding, or the like.

As mentioned above, the plunger head 22 is configured to substantially close the bottom opening 16 of the tubular body 12. Plunger head 22 includes one or more plunger seals or annular ribs 22a-c positioned about plunger head 22. Each rib 22a-c is spaced from an adjacent rib and is dimensioned to slidably and sealingly engage an inner wall 26b of tubular body 12. In embodiments, the inner wall 26b of reservoir 26 and plunger head 22 may be made of or include a lubricous material (e.g., polypropylene, polyethylene, etc.), such that plunger head 22 can press against inner wall 26b with sufficient force to provide a seal, while still be capable of sliding movement within tubular body 12.

Referring to FIGS. 4 and 5, microbial detection assembly 10 further includes retaining structures 24a and 24b. Retaining structures 24a and 24b are positioned to retain plunger head 22 within a predetermined area along the tubular body 12 during the microbial detection period. Retaining structure 24a is positioned in a central to bottom portion of the tubular body 12 and retaining structure 24b is positioned towards bottom end 16 of the tubular body 12.

Retaining structures 24a and 24b may be, for example, annular rings, which in turn, may be removable and/or adjustable. The annular rings are disposed, in a radial configuration, within the walls of tubular body 12. It is envisioned that retaining structures 24a and 24b may be fixedly secured at a predetermined position within tubular body 12. However, those skilled in the art will appreciate that retaining structures 24a and 24b may be adjustable to any position if desired. In alternate embodiments, retaining structures 24a and 24b may be injection molded nubs integrally formed within the walls of tubular body 12.

The microbial detection device 10 may be a, so called, "graduated" microbial detection device 10. In this configuration, the tubular body 12 may have indicia indicating to a clinician the distance the plunger head 22 has traveled during the microbial detection period. Additionally or alternatively the tubular body 12 may have indicia indicating to a clinician the amount of volume the reservoir 26 contains.

In use, as shown in FIGS. 4-5, a sample of blood 34 is deposited into reservoir 26 by way of syringe assembly 30 or any other type of substance transporting device. In particular, needle 32 of syringe assembly 30 is introduced into septum 18 and into reservoir 26, where a clinician expels some or all of the contents of syringe assembly 30. The blood sample 34 then mixes with the bacterial growth medium 28, which may be for example, a soy broth. If bacteria is present in the blood sample 34, bacterial growth takes place in the reservoir 26, resulting in generation of carbon dioxide within the headspace 26a. Headspace 26a includes a gas such as oxygen or nitrogen. The generated carbon dioxide results in a pressure increase within the reservoir 26, which, in turn, forces the plunger head 22 to move in a downward direction from a first position to a second position, as depicted by directional arrow "A" in FIG. 5. This, in turn, gives a visual indication to a clinician that bacterial growth has occurred within reservoir 26 of microbial detection assembly 10, thus identifying to a clinician that bacteria is present in the blood sample.

FIGS. 6 and 7 illustrate an alternative embodiment of the presently disclosed microbial detection assembly shown generally as 110. Microbial detection assembly 110 is substantially similar to microbial detection assembly 10 but includes a sensor 140. Microbial detection assembly 110, similarly to microbial detection assembly 10, includes a tubular body 112, a septum 118 and a plunger head 122, which together, define a reservoir 126. In this arrangement, the reservoir 126 is configured to contain a bacterial growth medium 128 having a head space 126a including oxygen and/or nitrogen, and a sample substance 134 (e.g., blood). When bacteria is present in the substance 134, carbon dioxide gas is generated as discussed above. As a result and depicted in FIG. 7, plunger head 122 moves within tubular body 112 towards bottom second end 116, indicating to a clinician that bacteria is present. Alternatively, plunger head 122 need not move and sensor 140 may provide an indication that carbon dioxide has been generated, thus indicating that the blood sample contains bacteria.

In embodiments, sensor 140 is disposed within the tubular body 112 of microbial detection assembly 110 to indicate to a clinician the levels of carbon dioxide within reservoir 126. Sensor 140 may be a colorimetric sensor, which in turn, responds to changes in carbon dioxide concentration emitted by bacteria by changing color or by changing fluorescence intensity. In embodiments, individual light sources, for example, colorimetric instruments, fluorometric instruments, and/or light emitting diodes may be used as an indicator for sensor 140.

Figure 8A:
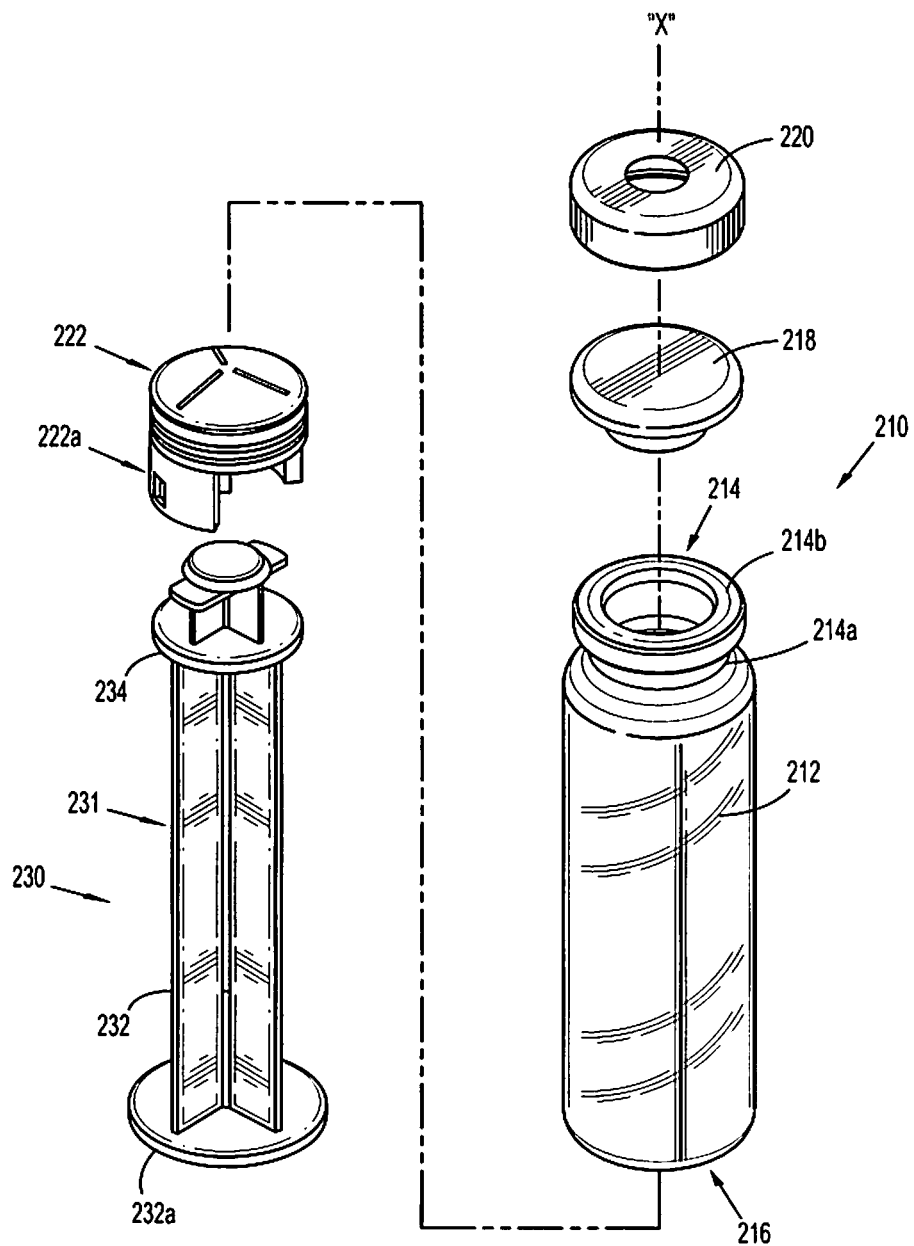
FIG. 8A is an exploded perspective view of another embodiment of the presently disclosed microbial detection assembly having a plunger head configured to receive a plunger rod.
Figure 8B:
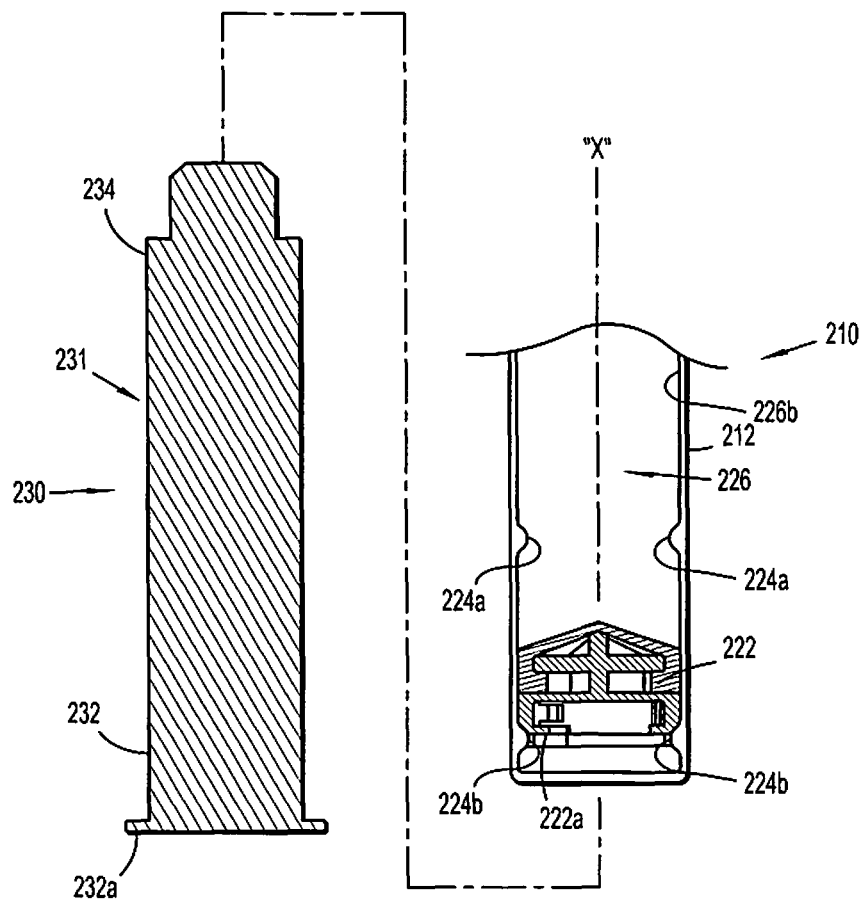
FIG. 8B is a side cross-sectional view of the microbial detection assembly of FIG. 8A showing a portion of a bottom end of a tubular body having the plunger head positioned therein and the plunger rod separated therefrom.
Figure 8C:
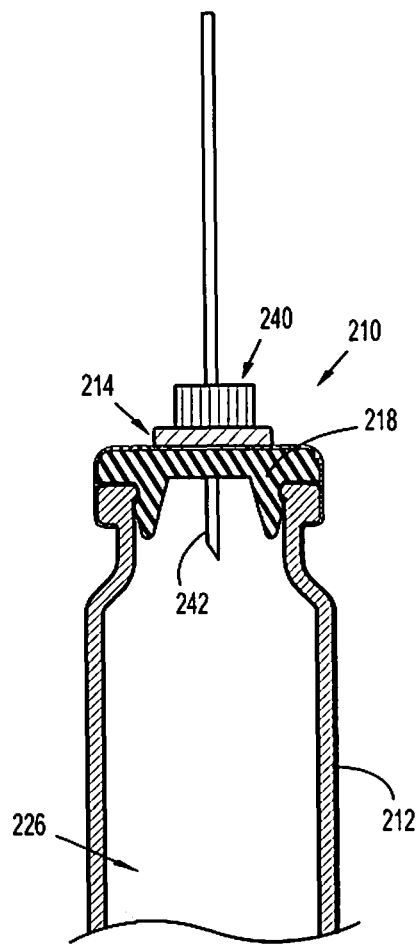
FIG. 8C is a side cross-sectional view of the microbial detection assembly of FIG. 8A showing a portion of a top end of the tubular body having a double-sided needle huh assembly mounted thereon.

FIGS. 8A-8C illustrate another embodiment of the presently disclosed microbial detection assembly shown generally as 210. Microbial detection assembly 210 includes a plunger head 222 configured to receive a plunger rod 230. Plunger head 222 and plunger rod 230 may be as described in U.S. Publication No. US 2008-0082055 A1 to Lloyd et al, the entire contents of which are hereby incorporated by reference herein. The plunger rod 230 has an elongate plunger shaft 231 configured and dimensioned for slidable disposition within tubular body 212 of microbial detection assembly 210. Tubular body 212, similarly to tubular body 12, includes retaining structures 224a and 224b for positioning plunger head 222 within a predetermined area along the tubular body 212 during the microbial detection period. Plunger shaft 231 includes a proximal end 232 which extends out of bottom end 216 of microbial detection assembly 210 and defines a finger engagement surface 232a. With the plunger head 222 disposed within the inner side wall 226b of the tubular body 212 along the longitudinal axis "X", the distal end 234 of plunger rod 230 is selectively connectable to a receiving channel 222a of plunger head 222. In use, a clinician can utilize microbial detection assembly 210 as a syringe assembly by simply attaching plunger rod 230 to tubular body 212, as described above, and applying a force to finger engagement surface 232a of plunger rod 230 to dispense a positive sample from within reservoir 226.

Referring to FIG. 8C, a clinician may attach a needle assembly 240 to the tubular body 212 to dispense the contents of reservoir 226 via the needle assembly 240. In one embodiment, a double-sided needle hub assembly 240 (as shown in FIG. 8C) is mounted on the top end 214 of tubular body 212 such that a proximal end of a needle 242 of needle assembly 240 penetrates septum 218. A distal end of needle 242 of needle assembly 240 may be blunted. Furthermore, during the dispensing of the contents of reservoir 226 via needle assembly 240 by a clinician, plunger head 222 may be movable along the longitudinal axis "X" beyond the first retaining structure 224a to a third position adjacent a neck portion 214a of the tubular body 212. The configuration shown in FIGS. 8A-8C allows a clinician to dispense a positive sample from reservoir 226 to a desired location, thus resulting in elimination of the use of a transfer syringe and a syringe needle, reducing the risk of accidental needle sticks.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for detecting microbial contents of a sample substance, comprising the steps of:
   providing a microbial detection device including:
      a tubular body defining a longitudinal axis and having first and second ends;
      a pierceable septum configured to seal the first end of the tubular body;
      a plunger head configured to substantially close the second end of the tubular body, the plunger head being spaced from the second end of the tubular body; and
      the plunger head, the pierceable septum, and the tubular body defining a reservoir having a first volume and including a bacterial growth medium, wherein the plunger head is movable within the tubular body in response to changes in pressure within the reservoir;
   depositing a sample substance in the reservoir of the microbial detection device; and
   observing the position of the plunger head within the tubular body to determine whether bacterial growth has taken place in the reservoir, wherein the reservoir has a second volume greater than the first volume when the plunger head has moved toward the second end of the tubular body in response to increased pressure within the reservoir as a result of bacterial growth.

2. The method for detecting microbial contents according to claim 1, further comprising the steps of:
   attaching a plunger rod to the plunger head;
   attaching a needle assembly to the septum; and
   applying at least a predetermined pressure to the plunger rod such that the plunger rod and the plunger head move along the longitudinal axis to dispense the medium and the sample substance from within the reservoir via the needle assembly.

* * * * *